United States Patent
Hart et al.

(10) Patent No.: US 6,626,922 B1
(45) Date of Patent: Sep. 30, 2003

(54) SURGICAL INSTRUMENTS WITH IMPROVED TRACTION

(75) Inventors: Charles C. Hart, Huntington Beach, CA (US); Donald L. Gadberry, Dana Point, CA (US); Eduardo Chi-Sing, Laguna Niguel, CA (US); Mark P. Ashby, Laguna Niguel, CA (US); Luis Urquidi, Laguna Hills, CA (US); Robert T. Jones, Laguna Hills, CA (US)

(73) Assignee: Applied Medical Resources Corporation, Laguna Hills, CA (US)

( * ) Notice: Subject to any disclaimer, the term of this patent is extended or adjusted under 35 U.S.C. 154(b) by 0 days.

(21) Appl. No.: 09/355,679

(22) PCT Filed: Feb. 3, 1998

(86) PCT No.: PCT/US98/02276

§ 371 (c)(1), (2), (4) Date: Sep. 9, 1999

(87) PCT Pub. No.: WO98/33437

PCT Pub. Date: Aug. 6, 1998

Related U.S. Application Data (60) Provisional application No. 60/037,077, filed on Feb. 3, 1997.

(51) Int. Cl.[7] .................. A61B 17/122; A61B 17/28
(52) U.S. Cl. ................................ 606/157; 606/207
(58) Field of Search .................. 606/51, 52, 142, 606/144, 148, 151, 157, 205–210, 119–122, 106, 158, 201, 204; 132/276–278; 81/418, 419, 421, 424.5

(56) References Cited

U.S. PATENT DOCUMENTS

| | | | | |
|---|---|---|---|---|
| 3,746,002 A | * | 7/1973 | Haller | 606/207 |
| 4,821,719 A | * | 4/1989 | Fogarty | |
| 4,955,897 A | * | 9/1990 | Ship | |
| 5,171,253 A | * | 12/1992 | Klieman | 606/158 |
| 5,681,336 A | | 10/1997 | Clement et al. | 606/159 |
| 5,685,854 A | | 11/1997 | Green et al. | 604/167 |
| 5,728,121 A | * | 3/1998 | Bimbo et al. | 606/207 |
| 6,126,671 A | * | 10/2000 | Richards et al. | 606/190 |

* cited by examiner

*Primary Examiner*—David O. Reip
(74) *Attorney, Agent, or Firm*—Morgan, Lewis & Bockius LLP

(57) ABSTRACT

A surgical instrument is adapted to contact tissue of a patient and to provide traction with the tissue in order to inhibit migration of the instrument relative to the tissue. The instrument may include a pair of opposing jaws with at least one of the jaws comprising a substrate having a particular surface facing the tissue, and a plurality of discrete elements disposed on the particular surface for increasing the traction of the instrument relative to the tissue. These discrete elements may include a multiplicity of granules, bristles, or projections and may be formed of materials having various properties such as hydrophilic characteristics. The discrete elements in the form of bristles can be oriented too so that the column strength of each bristle provides increased traction in a predetermined direction.

21 Claims, 9 Drawing Sheets

SURGICAL INSTRUMENTS WITH IMPROVED TRACTION

CROSS-REFERENCE TO RELATED APPLICATIONS

This is a Non-Provisional Application claiming the priority of Provisional Application Ser. No. 60/037,077 filed on Feb. 3, 1997, and entitled SURGICAL INSTRUMENTS WITH IMPROVED TRACTION.

BACKGROUND OF THE INVENTION

1. Field of the Invention

This invention relates generally to surgical instruments, and more specifically to surgical instruments which contact tissue and require traction with the tissue to inhibit migration of the instrument.

2. Discussion of the Prior Art

Most surgical instruments are intended to contact tissue, but for some instruments the traction developed between the instrument and the tissue is of particular importance. Instruments such as clips, clamps, retractors, stabilizers, and spreaders, for example, are intended to contact tissue and perform some mechanical function on the tissue. In these cases, the ability of the instrument to grip the tissue contacted is of concern. For example, when a clip is applied to a blood vessel with the intent of occluding that vessel, the occlusion is intended to occur at a predetermined location along the vessel. Although little force may be required to pinch and occlude the vessel, there may be a tendency for the clip to slide either axially or laterally along the vessel. Often this results from the back pressure of the blood in the vessel. If the clip slides radially of the vessel, it may fall off the vessel, leading to unintended blood flow. If the clip slides axially along the vessel, it will leave the predetermined location where the occlusion was intended.

The sliding of instruments relative to tissue is complicated by the fact that the tissue is typically covered with a body fluid, such as blood. As a consequence, the coefficient of friction between the tissue and the instrument tends to be relatively low.

In the past, clips and clamps have been provided with soft jaw inserts in order to reduce trauma to the conduit being occluded. For the most part, these inserts have been formed of a compliant material such as foam, and provided with a generally flat surface. The traction tending to hold the clip or clamp in place has been dictated by the well known formula for friction: $F = \mu N$, where F is the friction force resisting lateral movement, N is the normal force applied perpendicular to friction force, and $\mu$ is the coefficient of friction between the two surfaces.

In accordance with this formula, attempts have been made to increase the factor $\mu$ by providing inserts which have higher coefficients of friction with tissue. In spite of these efforts, traction has still been a problem since these coefficients cannot be increased significantly without damaging the vessel or other conduit being occluded.

Individual fibers in the form of loops have been applied to the inserts to improve traction. The traction in this case has relied, at least in part, on a mechanical interlock with the surface of the tissue, or other cohesive/adhesive phenomena.

As a practical consequence of this concern for traction, clamps have been applied to conduits such as vessels, and closed with a force sufficient to occlude the vessel. Where slippage has occurred, the tendency has been to increase the clamping force. With reference to the foregoing formula for friction, this increases the normal force N thereby increasing the friction or traction force F. Unfortunately, increases in the normal force N are not required for occlusion, which is the primary purpose of the clamp. Furthermore, high normal forces can create damage to a vessel, particularly the fragile endothelial lining of the vessel. What has been required for these surgical instruments is a structure which can provide a significant traction force without damage to the conduit or vessel.

SUMMARY OF THE INVENTION

In accordance with-the present invention, various structures are proposed for increasing the traction force without significantly changing the normal or occlusive force. In some cases, the traction force will be greater than the occlusive force, a condition that will be particularly appreciated for some instruments.

The surfaces providing increased traction will be advantageous in clips and clamps where there are opposing jaws which develop the normal force. Whether the improved traction is provided along one or both of the jaws can be a matter of choice.

The structures providing increased traction will also be applicable to spreaders where traction is appreciated on outwardly facing surfaces of opposing jaw members. Increased traction can be provided in the form of inserts for the jaws of clips, clamps, and retractors, or may take the form of webs providing a significant area of contact for the stabilization of organs. In the latter device, the normal force would be developed not between opposing jaws but relative to some other stationary stricture. For example, a stabilizer might be clamped to the sternum of the patient, or some other skeletal element, in order to provide a traction force against a beating heart in a bypass surgery.

DESCRIPTION OF PREFERRED EMBODIMENTS

Figure 1:
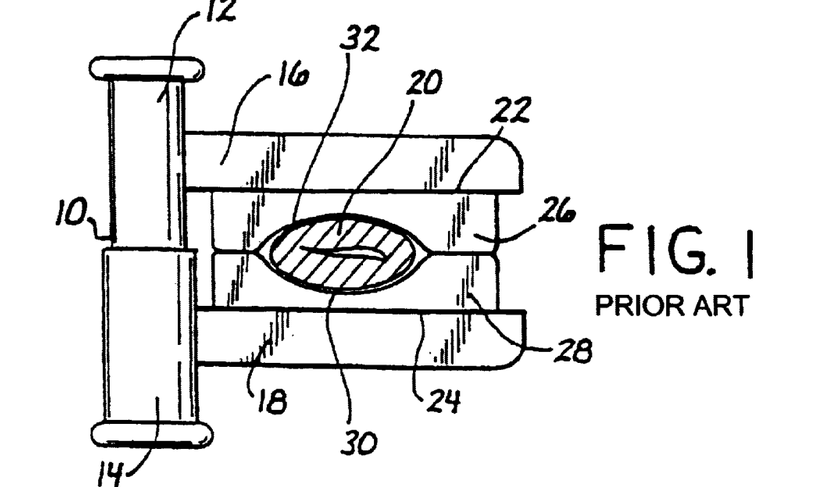
FIG. 1 is a side elevation view of a vascular clip of the prior art.

A vascular clip is illustrated, in FIG. 1 and designated by the reference numeral 10. The clip 10 is merely representative of many surgical instruments that contact tissue, instruments which can benefit from increased traction with the tissue. In addition to the clip 10, other instruments might include occlusion devices, such as clamps, as well as retractors, stabilizers, and spreaders. In each of these cases, it is desirable to maintain the instrument and the tissue in a generally fixed relationship without damaging the tissue. Thus, traction is of particular importance.

The clip 10 includes telescoping barrel portions 12 and 14, each of which is associated with one of a pair of opposing jaws 16 and 18. These jaws 16, 18 are biased into a proximal relationship so that a vessel 20 disposed between the jaws 16 and 18 is occluded. In the case of the clip 10, the jaws 16 and 18 have opposing surfaces 22 and 24, respectively, which face each other. Since these surfaces 22, 24 will typically be formed of a hard plastic material, it is common to cover the surfaces 22 and 24 with a soft, compliant material or pad 26 and 28 having a tissue-contacting surface 30 and 32, respectively.

In the past, these pads 26, 28 have reduced trauma to the vessel 20 but due to their smooth tissue-contacting surfaces 30, 32 have commonly provided little traction to resist, migration of the clip 10. The present invention appreciates the need to reduce trauma to the vessel 20, but also, importantly, to resist migration of the tissue-contacting instrument. The concept is well-suited to instruments that have opposing jaws such as clips, clamps, and retractors. In those instruments, the concept is advantageous whether the tissue-contacting surfaces face each other as is the case with clips, clamps, and retractors, or whether the tissue-contacting surfaces face away from each other as is the case with spreaders. the concept is also advantageous whether or only one of the opposing surfaces provides the increased traction. In some instruments, such as stabilizers, a single web providing a wide area of contact can benefit from the improved traction.

Figure 2:
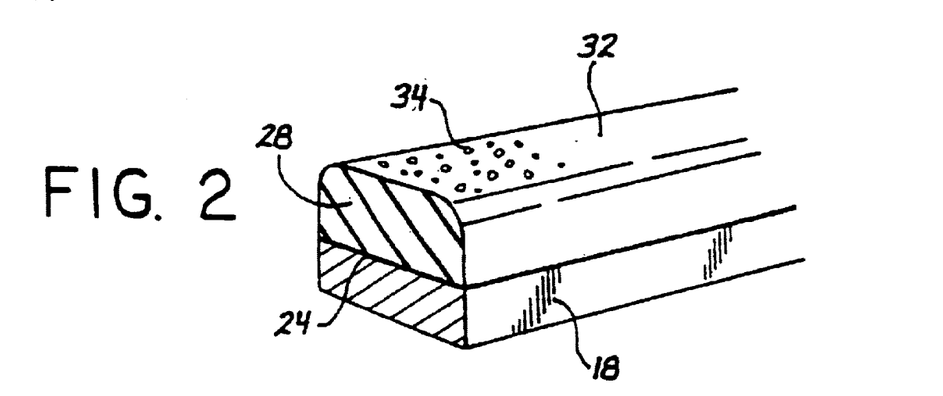
FIG. 2 is a perspective view, partially in cross section of a clip jaw and associated pad having of the present invention, having a tissue contacting service with granules

One embodiment of a tissue-contacting instrument with improved traction is illustrated in FIG. 2 where the jaw 18 is provided with the pad 28 having the tissue-contacting surface 32. In this embodiment, a multiplicity of granules 34 are disposed on the surface 32 in order to provide an irregular surface with increased traction. These granules 34 may be formed of sand or silica, or any other material providing an abrasive surface. These granules 34 are disposed to extend at least partially above the surface 32 in order to increase the coefficient of friction between the pad 28 and the tissue. It is believed that these granules 34 provide a mechanical interlock with the tissue thereby increasing the traction force and decreasing the possibility of migration.

The granules 34 will typically be formed of a relatively hard material, such as plastic or metal, and can be either applied by adhesive or otherwise molded into the surface 32. The granules 34 could similarly be applied directly to the jaw surface 24 in the absence of the pad 28. Thus, the irregular surface formed by the granules 34 provides a traction force which inhibits slippage of the clamping device, such as the clip 10, relative to the tissue, such as the vessel 20. The granules 34 may be provided with a coating which is hydrophilic. An anticoagulant, such as Heparin, may also be used as a coating.

Figure 3:
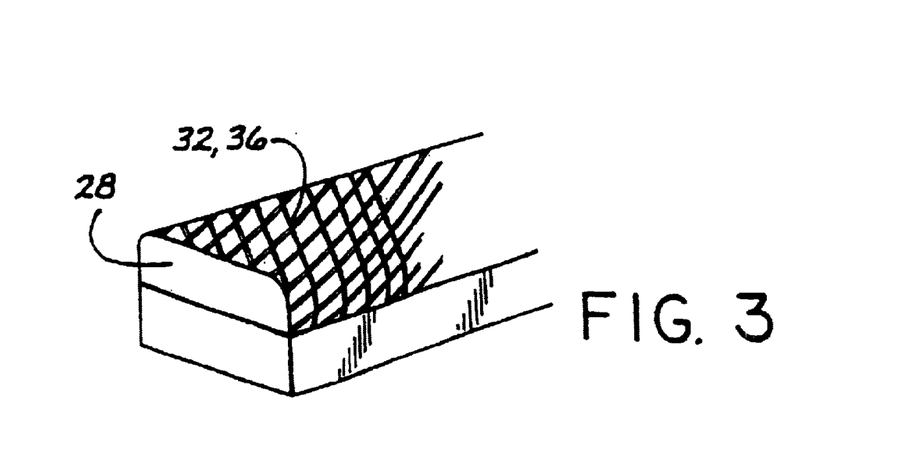
FIG. 3 is a perspective view similar to FIG. 2, including a pad and a mesh.

In the embodiment of FIG. 3, a mesh 36 is disposed over the tissue-contacting surface 32. In this case, the soft pad 28 forms a base for the mesh 36. The filaments forming the mesh 36 provide the tissue-contacting surface 32 with a rough, irregular configuration which varies with the thickness of the filaments. In the interstices of the mesh 36 where there are no filaments, the surface 32 has a thickness of zero. Where one filament overlies the surface, the mesh has the thickness of a single filament. And where the filaments overlap, the mesh 36 provides a thickness equivalent to twice the filament diameter. These variations in thickness enable the mesh 36 to grip the tissue, such as the vessel 20, to increase the traction force opposing slippage of the instrument. The mesh 36 can be formed of plastic or metal, and the mesh pattern can have any number of elements per square inch. The filaments forming the mesh pattern can be disposed at a right angle to each other, or at any other angles as desired. Typically, the mesh 36 will be attached to the pad 28 by an adhesive or by way of mechanical attachment such as an overmold procedure. The mesh 36 could be similarly attached directly to the jaw 18 and coated in the manner previously discussed.

Figure 4:
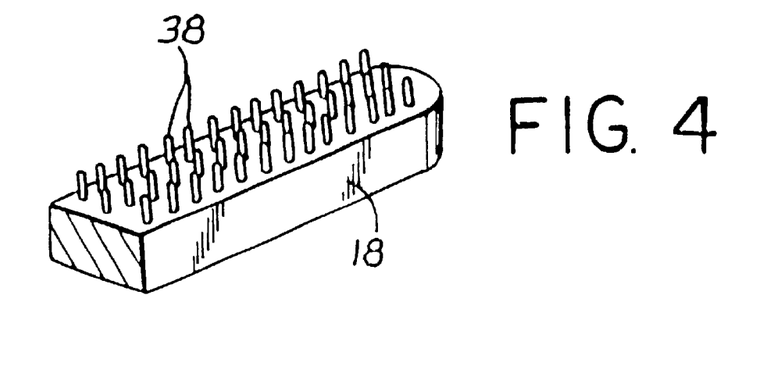
FIG. 4 is a perspective view partially in cross section and showing a pad with bristles providing improved traction.
Figure 5:
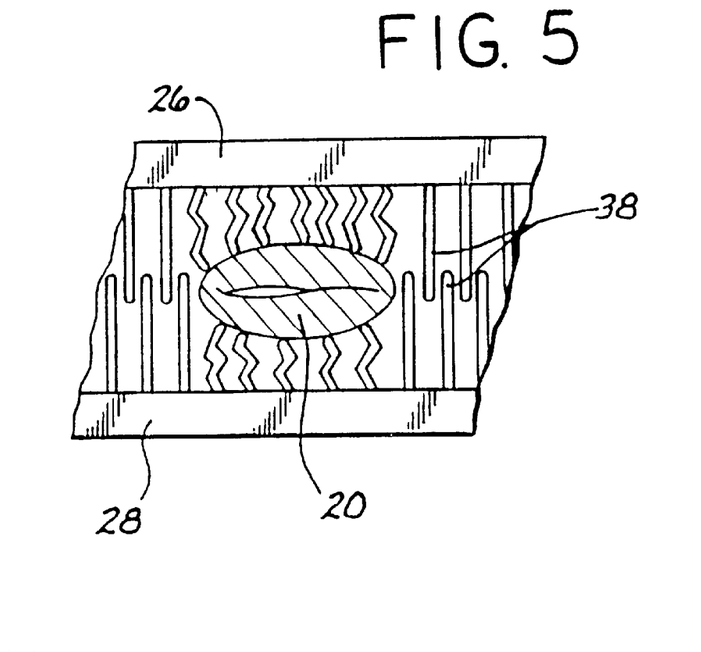
FIG. 5 is a cross-section view showing opposing pads and associated bristles engaging a vessel.
Figure 6:
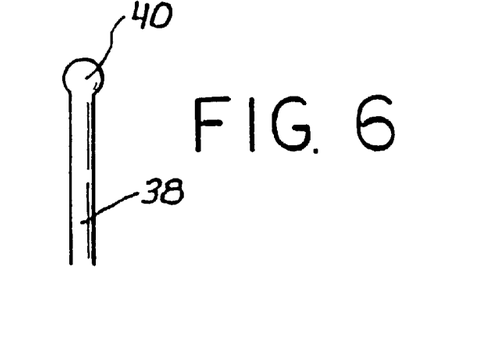
FIG. 6 is a front elevation view showing a single bristle with a bulb or enlargement at its end.

The provision of bristles 38 on or in the pad 28 can also improve traction as illustrated in the embodiments of FIGS. 4 and 5. In the embodiment of FIG. 4, the bristles 38 are molded directly into the plastic jaw 18. In this molding process, the bristles 38 can be individually molded into the jaw 18 or clumped together in groups of bristles 38 in the manner commonly associated with a toothbrush. The bristles can be upstanding in the manner best illustrated in FIG. 5. Where the bristles 38 contact tissue such as the vessel 20, they tend to axially crumple to develop an occlusive force. Laterally of the vessel 20, the bristles 38 resist slippage or movement of the vessel 20 relative to the instrument. FIG. 5 also illustrates that the bristles 38 can be molded into the atraumatic pads 26 and 28. The bristles 38 will commonly be formed from polyethylene or nylon. They may also be provided with bulbs or enlargements 40 on their ends as illustrated in FIG. 6. This configuration will further reduce trauma to the tissue or vessel 20. The bristles 38 can be coated in the manner previously discussed.

Figure 7:
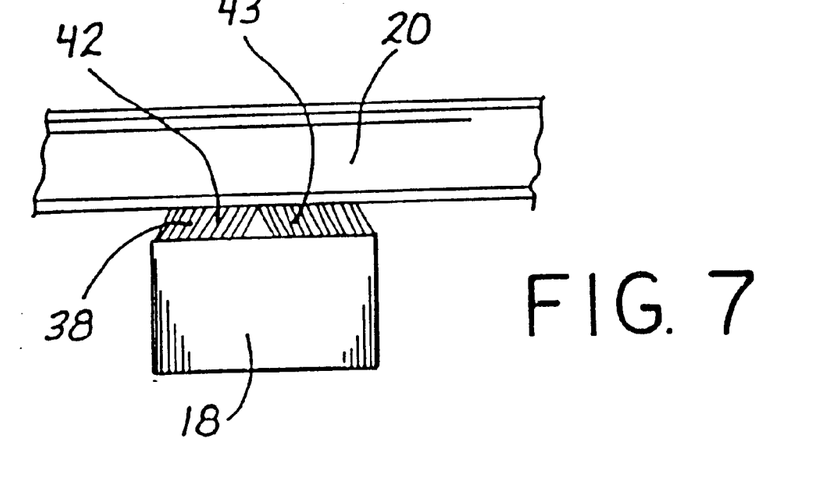
FIG. 7 is a front elevation view of an embodiment wherein the bristles are slanted to oppose movement of the jaw along the vessel.
Figure 8:
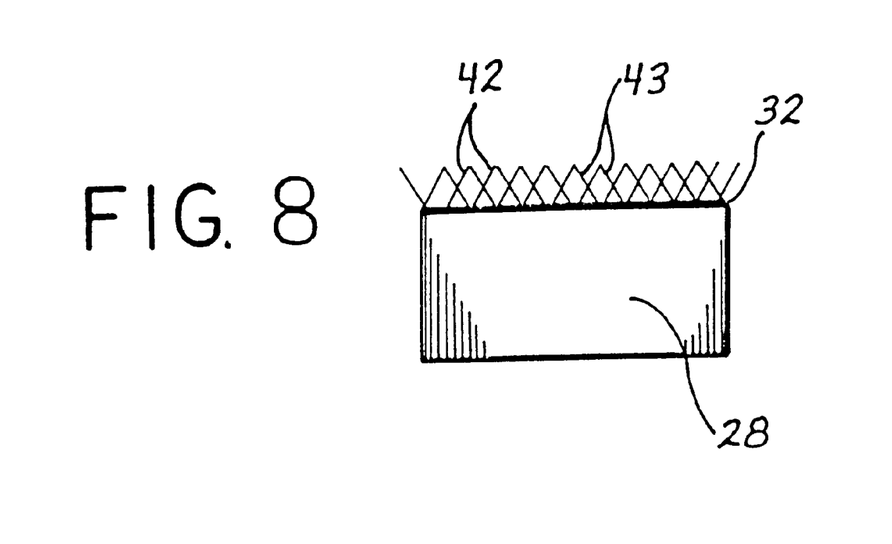
FIG. 8 is a front elevation view similar to FIG. 7 and illustrating intermingled bristles slanted in different directions.

FIG. 7 illustrates an embodiment where the bristles 38 are slanted to oppose movement of the jaw 18 along the axis of the conduit of vessel 20. Thus, the bristles 38 include a group 42 which is slanted to the right in FIG. 7 to oppose movement of the vessel 20 to the left. Similarly, a group 43 of the bristles 38 are slanted to the left to oppose movement of the vessel 20 to the right. Alternatively, the two groups 42 and 43 can be intermingled along the entire surface 32 of the pad 28 as illustrated in FIG. 8.

Figure 9:
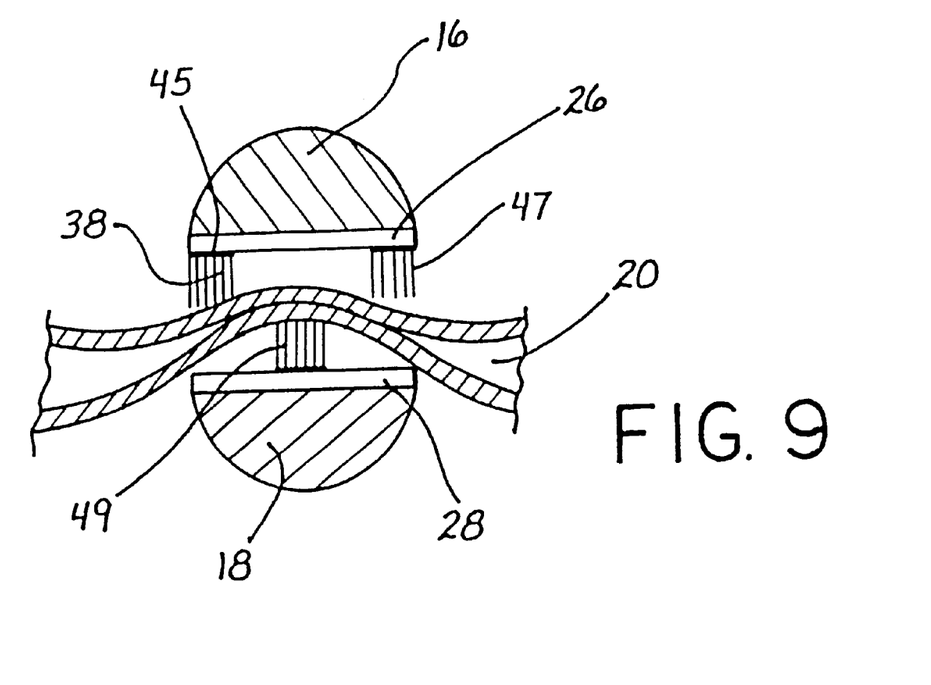
FIG. 9 is a front elevation view partially in cross section and illustrating opposing jaws with pads having bristles in bunches.

In the embodiment of FIG. 9, multiple clumps of the bristles 38, designated by reference numerals 45, 47, and 49, can be provided on the jaws 16, 18 with or without an opposing group of the bristles 38.

Figure 10:
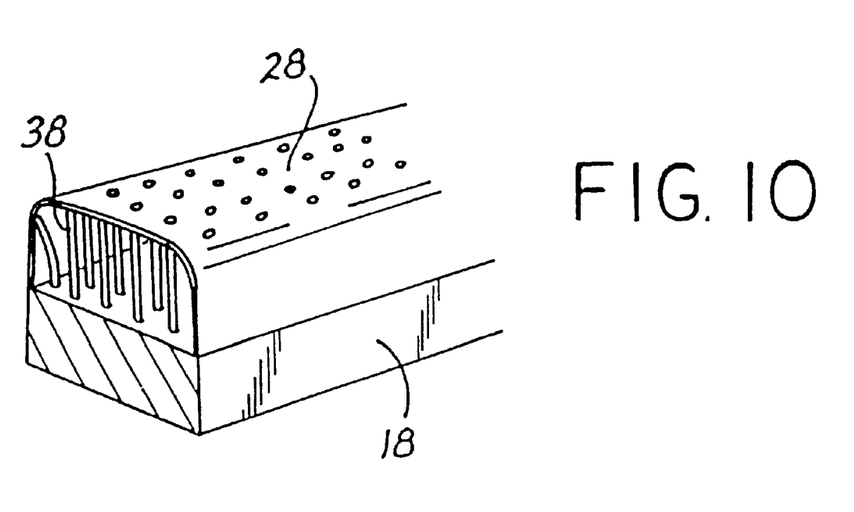
FIG. 10 is a perspective view of a further embodiment wherein the bristles are disposed in individual channels formed in a pad.
Figure 11:
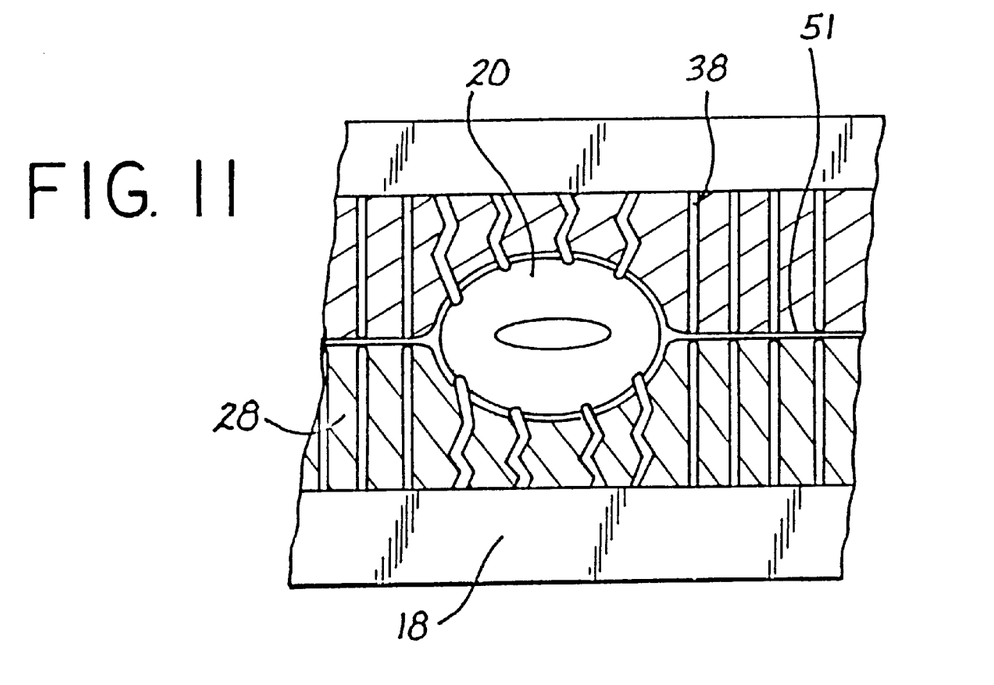
FIG. 11 is a side elevation view showing opposing jaws and the pad of FIG. 10 in a compression state.

FIGS. 10 and 11 illustrate a further embodiment where the bristles 38 are disposed in individual channels formed in the soft pad 28. Each of these channels is preferably provided with a diameter greater than that of the associated bristles 38 so that the clamping pressure initially compresses the foam pad 28 in order to contact the bristles 38. Further compression of the pad 28 will tend to form a mechanical interlock between the bristles 38 and the vessel 20, as shown in FIG. 11. As was the case with the mesh embodiments, the bristle embodiments can be formed by overmolding the bristles 38 with the pad material.

Figure 12:
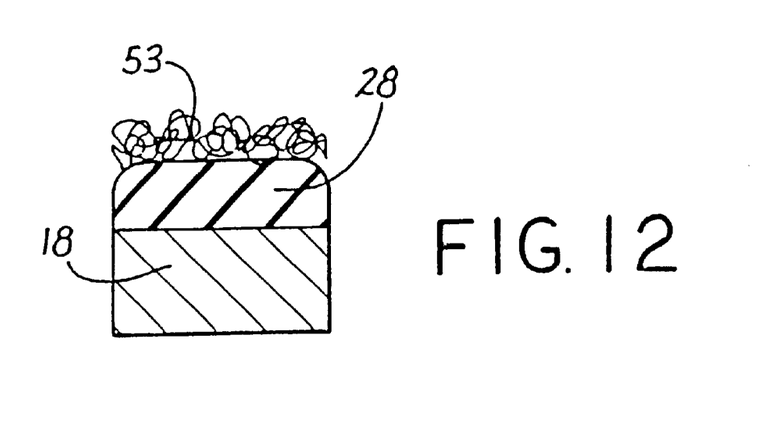
FIG. 12 is a front elevation view in cross section and showing a pad with a fiber surface.

FIG. 12 illustrates a further embodiment where the pad 28 is covered with a non-woven, wool-like material 53 is forming multiple loops. The loops can be continuous rather than discrete as is the case with the hook-and-loop configuration of the past. In such an embodiment, the wool-like material 53 is preferably provided with a soft configuration in order to enable the fiber to contour around the tissue or vessel 20. The fibers of the wool must nevertheless be sufficiently rigid to resist movement relative to the tissue or vessel 20. The resulting fibrous material can be bonded to the jaw 18 or pad 28. Alternatively, the pad 28 can be insert molded against the fibrous surface of the wool-like material 53. The fibrous material 53 can be coated in the manner previously described.

Figure 13:
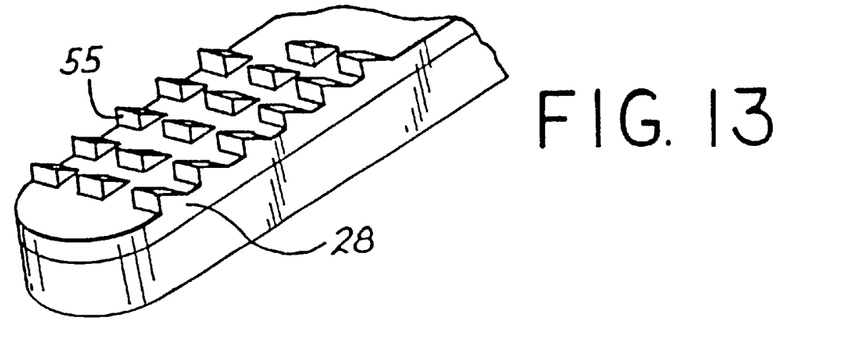
FIG. 13 is a perspective view of a jaw and pad having molded projections.
Figure 14:
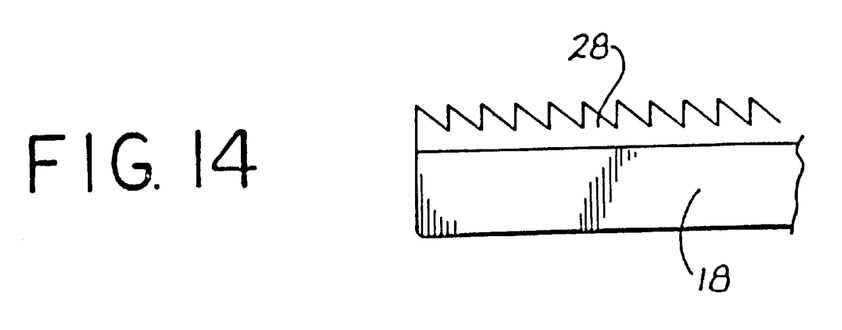
FIG. 14 is a side elevation view of a pad with projections in a saw-tooth shape.

The pads or inserts 26, 28 can also be molded to form multiple projections 55 arranged in a waffle pattern, such as that illustrated in FIGS. 13 and 14. Within the pattern, projections 55 can be the same, similar, or widely different. Some projections will have a common, cross-sectional shape throughout their entire length. Other projections may extend to a point or reduced cross-sectional area as would be the case with a pyramid shape. The cross-sectional shape can also vary widely. For example, the projections 55 may have a cross-section that is circular, polygonal, or any irregular shape.

The projections 55 can also be angled so that in a side view, such as that illustrated in FIG. 14, they have a saw-tooth shape. With this configuration, movement of tissue against the saw teeth would be opposed with a greater force than movement of tissue along the same teeth. In this manner, slippage can be inhibited by high traction in one direction and facilitated by low traction in the opposite direction.

Figure 15:
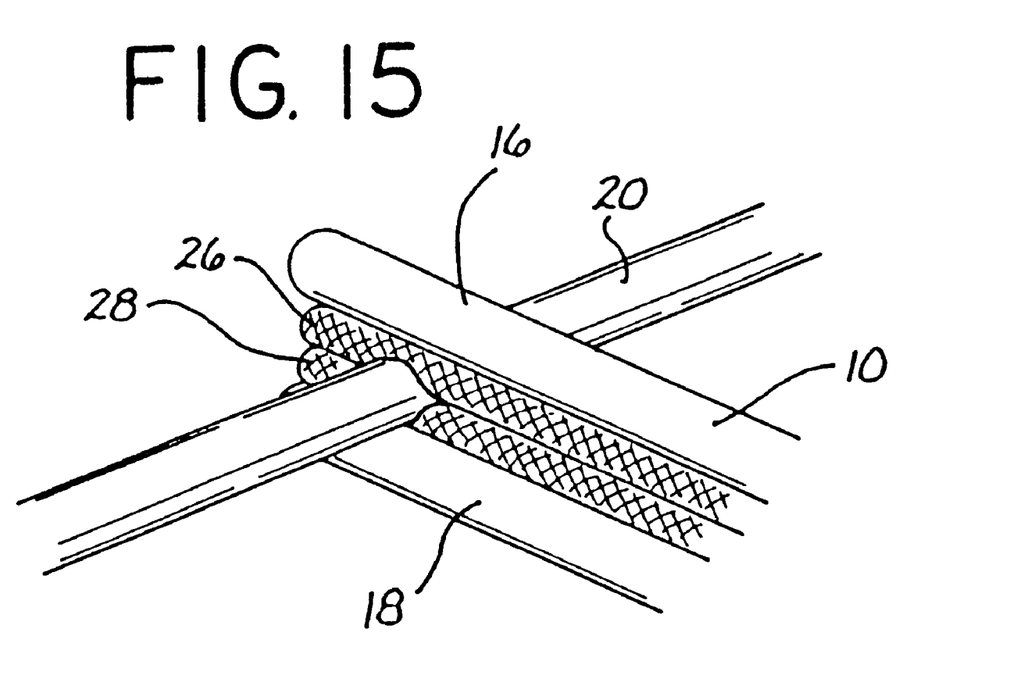
FIG. 15 is a perspective view of a clip with opposing jaws and associated atraumatic pads of a hydrophilic material covered by a mesh.

In FIG. 15, the clip 10 is illustrated with its opposing jaws 16, 18 and associated atraumatic pads 26, 28. In this case, the pads 26, 28 are formed of a hydrophilic material such as expanded polyethylene. This material directly contacts the moist tissue, such as the vessel 20, and withdraws moisture from the tissue, leaving a dryer surface and a resulting higher coefficient of friction between the tissue or vessel 20 and the pads 26, 28. With a higher coefficient of friction, slippage of the clip 10 on the vessel 20 is substantially inhibited without an increase in the occlusive force applied by the jaws 16, 18. These hydrophilic properties can also be achieved by coating the pads 26, 28 with a hydrophilic material.

Figure 16:
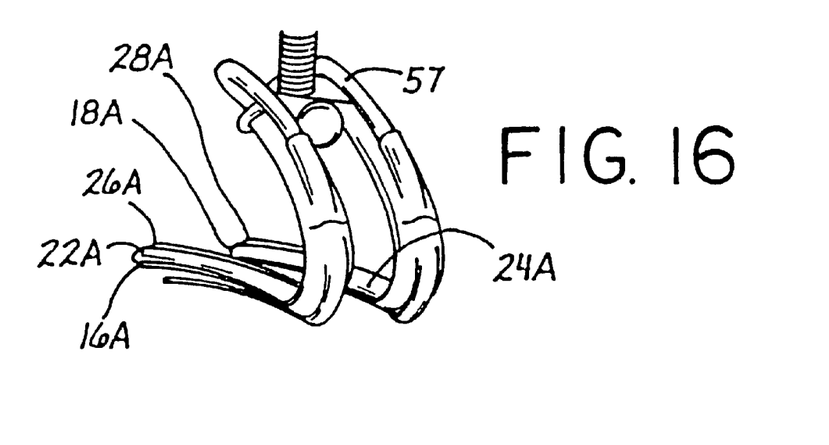
FIG. 16 is a perspective view of a retractor having opposing jaws with improved traction.
Figure 17:
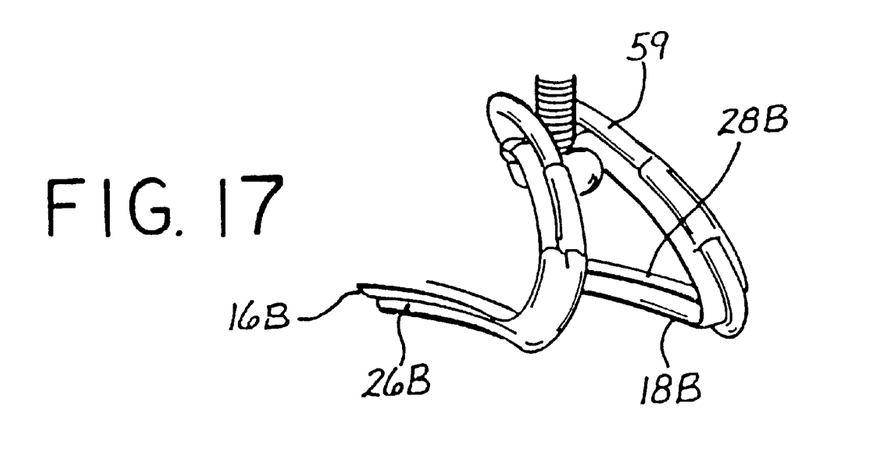
FIG. 17 is a perspective view of a spreader having jaws with improved traction.

Although the foregoing embodiments providing increased traction have been disclosed primarily with respect to clips and clamps, it will be apparent that many other embodiments of the invention can be equally advantageous as in the case of a retractor 57, illustrated in FIG. 16, and a spreader 59 illustrated in FIG. 17. As was the case with the occlusion instruments, such as the clip 10, the retractor 57 of FIG. 16 includes opposing jaws 16A and 16B with jaw surfaces 22A and 24A which face each other. These surfaces 22A, 24A can be provided with pads 26A, 28A, or otherwise coated or structured in accordance with any of the foregoing embodiments.

Referring now to FIG. 17, it will be noted that the spreader 59 also includes opposing jaws 16B and 18B. However, in this embodiment, the jaw surfaces face outwardly rather than toward each other. Thus, in the case of the spreader 59, the traction-increasing structures, such as pads 26B and 28B, face outwardly of the respective jaws 16B and 18B.

Figure 18:
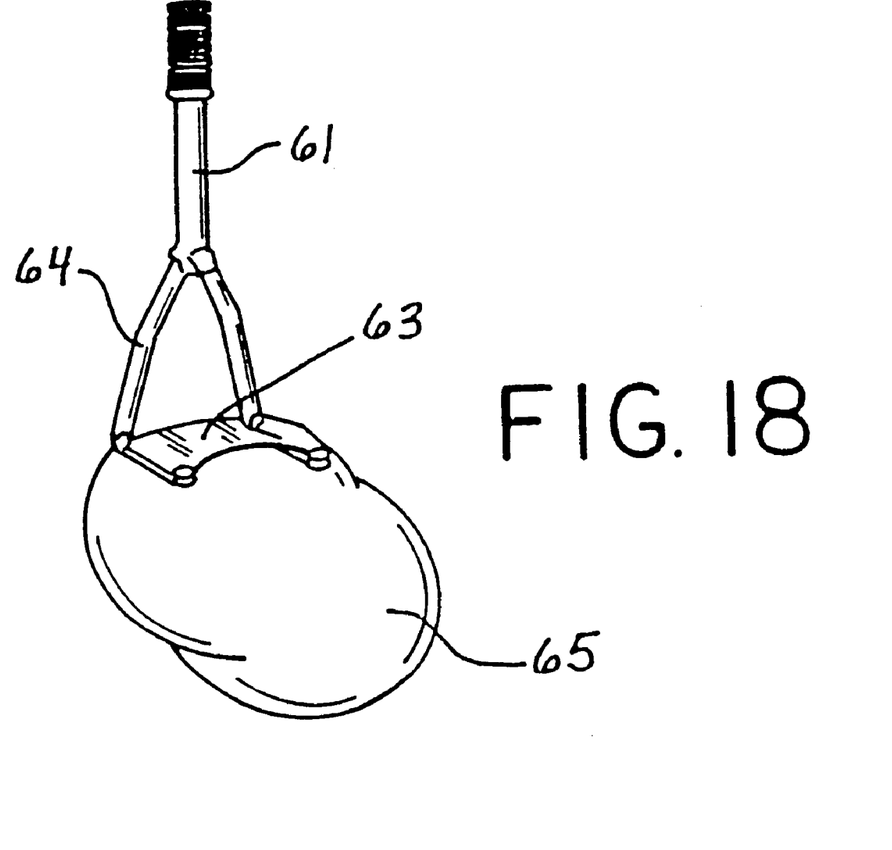
FIG. 18 is a perspective view of a stabilizer including a web having improved traction.

A stabilizer is illustrated in FIG. 18 and designated by the reference numeral 61. This stabilizer 61 includes a web 63 which is stretched between opposing areas of a plastic support 64. The web 63 can be formed from any of the high-traction materials previously discussed. In operation, this web 63 is held against an organ, such as a beating heart 65, in order to stabilize or otherwise hold the organ in a generally fixed location during surgery.

In all of the foregoing embodiments, the surgical instrument, such as the clip 10, is provided with a structure which increases the coefficient of friction with the tissue, or otherwise develops a mechanical interlock with the tissue so that slippage of the instrument is inhibited. In all cases, the structure can be coated with a thrombogenic, hydrophilic, or similar materials in order to facilitate the objectives of the instrument. Whether the traction structure is provided on one or both of an opposing pair of jaws, as in the case of the clip 10, or formed as a single element as in the case of the stabilizer 61, it will increase traction between the instrument and the tissue in order to inhibit relative movement therebetween.

It will be understood that many other modifications can be made to the various disclosed embodiments without departing from the spirit and scope of the concept. For example, various sizes of the surgical device are contemplated as well as various types of constructions and materials. It will also be apparent that many modifications can be made to the configuration of parts as well as their interaction. For these reasons, the above description should not be construed as limiting the invention, but should be interpreted as merely exemplary of preferred embodiments. Those skilled in the art will envision other modifications within the scope and spirit of the present invention as defined by the following claims.

What is claimed is:

1. A surgical instrument adapted to contact tissue of a patient and to provide traction with the tissue so as to inhibit migration of the instrument relative to the tissue, the surgical instrument comprising:

a substrate formed of a resilient material and having a particular surface adapted to face the tissue of the patient;

a multiplicity of bristles having a column strength and extending outwardly of the particular surface in a slanted relationship with the particular surface, the bristles being adapted for disposition relative to the tissue in a contacting relationship with the tissue; and each of the bristles having a generally straight configuration so that the force of the bristles on the tissue is enhanced by the column strength of the bristles thereby providing increased traction between the instrument and the tissue.

2. A surgical instrument adapted to contact tissue of a patient and to provide traction with the tissue so as to inhibit migration of the instrument relative to the tissue, the surgical instrument comprising:

a substrate formed of a resilient material and having a particular surface adapted to face the tissue of the patient;

a multiplicity of bristles extending outwardly of the particular surface, each of the bristles having a column strength, the bristles being adapted for disposition relative to the tissue in a contacting relationship with the tissue;

each of the bristles having a generally straight configuration so that the force of the bristles on the tissue is enhanced by the column strength of the bristles thereby providing increased traction between the instrument and the tissue;

a first group of the bristles disposed at a first angle to the particular surface of the substrate;

a second group of the bristles disposed at a second angle to the particular surface of the substrate; and the first angle being different than the second angle.

3. The surgical instrument recited in claim 2 wherein the first group of the bristles is spaced from the second group of the bristles.

4. The surgical instrument recited in claim 3 wherein the first group of the bristles is intermingled with the second group of the bristles.

5. A surgical instrument adapted to contact tissue of a patient and to provide traction with the tissue so as to inhibit migration of the instrument relative to the tissue, the surgical instrument comprising:

a substrate formed of a resilient material and having a particular surface adapted to face the tissue of the patient;

a multiplicity of bristles extending outwardly of the particular surface, each of the bristles having a column strength, the bristles being adapted for disposition relative to the tissue in a contacting relationship with the tissue;

each of the bristles having a generally straight configuration so that the force of the bristles on the tissue is enhanced by the column strength of the bristles thereby providing increased traction between the instrument and the tissue;

a first group of the bristles forming a first discrete patch of the bristles;

a second group of the bristles forming a second discrete patch of the bristles; and the first patch of bristles being spaced from the second patch of bristles.

6. A surgical instrument adapted to contact tissue of a patient and to provide traction with the tissue so as to inhibit migration of the instrument relative to the tissue, the surgical instrument comprising:

a substrate formed of a resilient material and having a particular surface adapted to face the tissue of the patient;

a multiplicity of bristles extending outwardly of the particular surface, each of the bristles having a column strength, the bristles being adapted or dispositioned relative to the tissue in a contacting relationship with the tissue; and each of the bristles being embedded in the substrate and having a generally straight configuration so that the force of the bristles on the tissue is enhanced by the column strength of the bristles thereby providing increased traction between the instrument and the tissue.

7. A surgical instrument adapted to contact tissue of a patient and to provide traction with the tissue so as to inhibit migration of the instrument relative to the tissue, the surgical instrument comprising:

a substrate formed of a resilient material and having a particular surface adapted to face the tissue of the patient;

a multiplicity of bristles extending outwardly of the particular surface, each of the bristles having a column strength, the bristles being adapted for disposition relative to the tissue in a contacting relationship with the tissue;

at least one of the bristles having a fixed end and a free end; and a bulb formed on said free end.

8. A surgical instrument adapted to contact tissue of a patient and to provide traction with the tissue so as to inhibit migration of the instrument relative to the tissue, the surgical instrument comprising:

a support formed of a generally rigid material;

a pad disposed in fixed relationship with the support and having a particular surface facing away from the support, the particular surface having first traction characteristics with the tissue; and a multiplicity of loops formed by a single fiber arranged in random configuration and disposed outwardly of the particular surface of the pad, the loops providing a tissue-contacting surface with an irregular configuration, the tissue-contacting surface being adapted to provide the pad with second traction characteristics with the tissue.

9. The surgical instrument recited in claim 8 wherein the loops are embedded in the pad.

10. A surgical instrument adapted to contact tissue of a patient and to provide traction with the tissue, the surgical instrument comprising:

a support having a length extending in a longitudinal direction, and a width extending in a lateral direction;

a pad formed of a resilient material and disposed in fixed relationship with the support, the pad having a particular surface facing away from the support, the particular surface having first traction characteristics with the tissue;

a multiplicity of discrete elements disposed to extend outwardly of the particular surface of the pad and to provide a tissue contacting surface; and the discrete elements forming multiple projections each having an axis which extends generally along the length of the support without any component in the lateral direction, to provide the tissue-contacting surface with second traction characteristics greater than the first traction characteristics.

11. The surgical instrument recited in claim 10 wherein the length of the support extends between a proximal end and a distal end, and the projections extend distally along the length of the support.

12. A surgical instrument adapted to contact tissue of a patient and to provide traction with the tissue, the surgical instrument comprising:

a support structure;

a resilient pad having a fixed relationship with the support structure;

portions of the pad defining an outer surface of the pad, the outer surface being adapted to contact the tissue; and at least the portions of the pad having hydrophilic characteristics for withdrawing moisture from the tissue to increase the traction between the instrument and the tissue, wherein the outer surface of the pad has an irregular configuration and the portions of the pad include a multiplicity of granules.

13. A surgical instrument adapted to contact tissue of a patient and to provide traction with the tissue, the surgical instrument comprising:

a support structure;

a resilient pad having a fixed relationship with the support structure;

portions of the pad defining an outer surface of the pad, the outer surface being adapted to contact the tissue; and at least the portions of the pad having hydrophilic characteristics for withdrawing moisture from the tissue to increase the traction between the instrument and the tissue, wherein the portions of the pad form a multiplicity of discrete elements adapted to contact the tissue.

14. The surgical instrument recited in claim 13 wherein the discrete elements are integral with the pad.

15. The surgical instrument recited in claim 14, wherein:

the pad has a generally planar configuration; and the discrete elements are disposed at an angle to the plane of the pad.

16. The surgical instrument recited in claim 13 wherein the discrete elements include a multiplicity of loops formed by a single, continuous fiber.

17. The surgical instrument recited in claim 13 wherein the discrete elements include at least one fiber having a generally straight configuration throughout its length and being adapted to extend into contact with the tissue.

18. A surgical instrument adapted to function as a retractor, comprising:

a pair of elongate jaws having inner surfaces which face toward each other and outer surfaces which face away from each other;

at least one pad disposed on an inner surface of one of the jaws and being formed of a first material having resilient characteristics; and a tissue-contacting member formed of a second material having a tissue-contacting surface with an irregular configuration for enhancing the traction between the surgical instrument and the tissue, wherein the tissue contacting member includes a plurality of discrete elements, said pad having a generally planar configuration, and the discrete elements being disposed at an angle to the plane of the pad.

19. A surgical instrument adapted to function as a spreader, comprising:

a pair of elongate jaws having inner surfaces which face toward each other and outer surfaces which face away from each other;

at least one pad disposed on an outer surface of one of the jaws and being formed of a first material having resilient characteristics; and a tissue-contacting member formed of a second material having a tissue-contacting surface with an irregular configuration for enhancing the traction between the surgical instrument and the tissue, wherein the tissue contacting member includes a plurality of discrete elements, said pad having a generally planar configuration, and the discrete elements being disposed at an angle to the plane of the pad.

20. A surgical instrument adapted to function as an organ stabilizer, comprising:

a pair of elongate jaws having inner surfaces which face toward each other and outer surfaces which face away from each other;

at least one pad formed of a first material having resilient characteristics and being disposed on one of the inner and outer surfaces of one of the jaws;

a tissue-contacting member formed of a second material having a tissue-contacting surface with an irregular configuration for enhancing the traction between the surgical instrument and the tissue; wherein the pad is disposed to extend between the inner surfaces of the jaws to form a web.

21. A surgical instrument adapted to contact tissue of a patient and to provide atraumatic traction with the tissue, the surgical instrument comprising:

a support structure;

a pad disposed on the support structure and being formed of a first material having a first surface adapted to have a space relationship with the tissue;

a tissue-contacting member formed of a second material and having a second surface adapted to have a contacting relationship with the tissue;

said second surface including a plurality of fibers of generally straight configuration throughout their length adapted to contact said tissue to facilitate traction with the tissue; and the first material of the pad having resilient characteristics to inhibit trauma to the tissue.

* * * * *